United States Patent
Vialle et al.

(10) Patent No.: US 12,432,538 B2
(45) Date of Patent: Sep. 30, 2025

(54) ASSISTANCE IN CONTROLLING THE SPREAD OF A DISEASE, USING NETWORKED DEVICES

(71) Applicant: Orange, Issy-les-Moulineaux (FR)

(72) Inventors: Stéphane Vialle, Chatillon (FR); Guy Vidal, Chatillon (FR)

(73) Assignee: Orange, Issy-les-Moulineaux (FR)

( * ) Notice: Subject to any disclaimer, the term of this patent is extended or adjusted under 35 U.S.C. 154(b) by 434 days.

(21) Appl. No.: 17/915,395

(22) PCT Filed: Mar. 25, 2021

(86) PCT No.: PCT/FR2021/050514
§ 371 (c)(1),
(2) Date: Sep. 28, 2022

(87) PCT Pub. No.: WO2021/198592
PCT Pub. Date: Oct. 7, 2021

(65) Prior Publication Data
US 2023/0125123 A1 Apr. 27, 2023

(30) Foreign Application Priority Data

Mar. 30, 2020 (FR) ..................................... 2003146

(51) Int. Cl.
*H04W 4/90* (2018.01)
*G16H 50/80* (2018.01)
(Continued)

(52) U.S. Cl.
CPC .............. *H04W 4/90* (2018.02); *G16H 50/80* (2018.01); *H04W 4/021* (2013.01); *H04W 4/029* (2018.02)

(58) Field of Classification Search
CPC ....... H04W 4/021; H04W 4/029; H04W 4/90; G16H 50/80
(Continued)

(56) References Cited

U.S. PATENT DOCUMENTS 1,513,486 A * 10/1924 Burdick ................. G07D 11/10
  400/636
9,848,312 B2 * 12/2017 Sundel .................. H04W 4/021
(Continued)

OTHER PUBLICATIONS

Ikki Ohmukai et al., "Tracing patients' PLOD with mobile phones: Mitigation of epidemic risks through patients' locational open data", arxiv.org, Cornell University Library, 201 Olin Library Cornell University Ithaca, NY 14853, Mar. 13, 2020.
(Continued)

*Primary Examiner* — Jean A Gelin
(74) *Attorney, Agent, or Firm* — Knobbe, Martens, Olson & Bear, LLP (57) ABSTRACT

A method of assistance in controlling the spread of a contagious disease, using networked devices, is disclosed. The method includes upon receiving data relating to infection by the disease of a first user of a first mobile terminal, obtaining a list including data of successive geographical positions of the first terminal over a predetermined period of time, and estimating a region at risk of infection by the first user, and for a second terminal available to a second user: obtaining a geographical position datum of the second terminal during the period of time, and comparing the geographical position of the second terminal to the region at risk by the datum of the second terminal, in the event of a coincidence between the geographical position of the second terminal and the region at risk, activating a human-machine interface connected to the second terminal to inform the second user of a risk.

19 Claims, 5 Drawing Sheets

(51) Int. Cl.
 *H04W 4/021* (2018.01)
 *H04W 4/029* (2018.01)
(58) Field of Classification Search
 USPC ....................................................... 455/404.1
 See application file for complete search history.

(56) References Cited

U.S. PATENT DOCUMENTS

| | | | |
|---|---|---|---|
| 9,945,672 B2* | 4/2018 | Balasubramanian | ........................ A61B 5/0002 |
| 10,049,183 B2* | 8/2018 | Noh | ........................ G16H 20/00 |
| 10,290,377 B2* | 5/2019 | Bastide | ................. G16H 50/30 |
| 10,356,741 B2* | 7/2019 | Wigren | ................. H04W 24/10 |
| 11,264,130 B2* | 3/2022 | Lee | ........................ G16H 80/00 |
| 11,309,091 B2* | 4/2022 | Singh | ..................... G16H 50/80 |
| 11,645,552 B2* | 5/2023 | Bastide | .................... G06N 5/04 706/11 |
| 12,154,692 B2* | 11/2024 | Sadilek | ................. G06N 20/00 |
| 2015/0019235 A1* | 1/2015 | Roychowdhury | ..... G06Q 40/08 705/2 |
| 2016/0132652 A1 | 5/2016 | Chapman | |
| 2019/0252078 A1 | 8/2019 | Schubert et al. | |

OTHER PUBLICATIONS

International Search Report for PCT/FR2021/050514 dated Jul. 7, 2021 by European Patent Office.

\* cited by examiner

ASSISTANCE IN CONTROLLING THE SPREAD OF A DISEASE, USING NETWORKED DEVICES

CROSS-REFERENCE TO RELATED APPLICATIONS

This application is filed under 35 U.S.C. § 371 as the U.S. National Phase of Application No. PCT/FR2021/050514 entitled "ASSISTANCE IN CONTROLLING THE SPREAD OF A DISEASE, USING NETWORKED DEVICES" and filed Mar. 25, 2021, and which claims priority to FR 2003146 filed Mar. 30, 2020, each of which is incorporated by reference in its entirety.

BACKGROUND

Field

This disclosure relates to the field of devices communicating in a network in particular here to assist with limiting the spread of a contagious disease, for example viral.

Description of the Related Technology

To fight against the spread of a virus, such as COVID19 in particular, it would be conceivable to track the current position of the mobile terminal of an infected person on a geographical map, based on the person's successive geolocation coordinates. This movement tracking can then be communicated to third parties, so that they can avoid areas traversed by the mobile terminal of the infected user.

Such an embodiment has a disadvantage linked in particular to the lack of confidentiality represented by disclosing movement data to third parties, these data being personal and specific to the infected user. In addition, this implementation only allows limiting possible future infections by the infected person, without making it possible to alert third parties that the person could have encountered, and therefore infected, before being diagnosed as infected. Finally, if this implementation were to be applied on a large scale, the massive communication of geolocation coordinates, from a potentially very large number of mobile terminals of infected people to an even greater number of mobile terminals to be informed, could overload the telecommunications networks.

SUMMARY OF DISCLOSURE

This description improves the situation.

To this end, it proposes a method, implemented by networked devices, for assisting in controlling the spread of a contagious disease, the method comprising:
  upon receiving data relating to infection by the disease of a first user of a first mobile terminal, obtaining a list comprising at least successive geographical position data of the first terminal over a predetermined period of time, and estimating from said list at least one region at risk of infection by the first user, and
  for a second terminal available to a second user:
  obtaining at least one geographical position datum of the second terminal during at least said period of time, and comparing the geographical position of the second terminal to the region at risk by means of said geographical position datum of the second terminal,
  in the event of a coincidence, according to a chosen criterion, between the geographical position of the second terminal and the region at risk, activating a human-machine interface connected to the second terminal in order to inform the second user of a risk of infection.

Thus, estimating the (general) region at risk makes it possible to avoid retaining the precise geographical positions occupied by the user of the first terminal, and thus protect the user's personal data. The estimate of this general region at risk can then be communicated to third-party terminals (such as the aforementioned second terminal) with relatively little data needed to define this region. It may be, for example, a city or a city district, or only a few districts of this city, etc. The small size of the messages transmitted to third-party terminals such as the aforementioned second terminal thus makes it possible to preserve bandwidth in the communication network through which these messages travel. In addition, as this implementation makes it possible to alert third parties who may have been infected by the user of the first terminal, these third parties can take precautions to avoid infecting in turn those around them, and can quickly seek medical advice from a health professional for an early diagnosis (by medical tests, auscultation, or other means).

In one embodiment of this method:
  a server obtains said infection data from the first user with the list of the successive geographical position data of the first terminal in order to estimate said region at risk, and sends to the second terminal a notification comprising at least one datum relating to said region at risk, and
  as the second terminal stores its geographical position data for at least said period of time, the second terminal:
  ignores the notification if there is no coincidence between its geographical position during said period of time and the region at risk, or
  activates said human-machine interface in the event of a coincidence, according to the chosen criterion, between its geographical position during said period of time and the region at risk.

The aforementioned notification may typically be sent in push mode to several third-party terminals, such as the aforementioned second terminal. This notification indicates the general region at risk, therefore with little data needed as indicated above (name of city, name of city district, or other). The third-party terminals can simply ignore this notification if they are not concerned by the region at risk indicated in the notification (because they are located in another city or another district), or, otherwise, can check the coincidence more precisely according to the chosen criterion mentioned above, between their position and the region at risk, before triggering activation of the human-machine interface alerting their user of the risk of infection.

In one embodiment, the first terminal is configured for:
  storing in memory said list comprising the successive geographical position data of the first terminal over the predetermined period of time, according to a first in/first out type of mode (usually called FIFO), and
  sending the infection data of the first user to the server, along with the data from said stored list.

This type of storage makes it possible to preserve the memory capacity of the terminal by only keeping this data over a sliding time window, of which the duration may correspond, for example, to the incubation period of the disease plus a few days for safety.

In one embodiment, the list comprises:
  successive geographical position data of the first terminal, obtained by geolocation, and respective identifiers of radio frequency beacons detected near the first terminal.

Such an implementation makes it possible to determine the general region at risk based on geographical position data, and to refine the risk determination by studying the identifiers of radio frequency beacons. These radio frequency beacons may be, for example, Wi-Fi, Bluetooth, or other types of access point hotspots, or even domestic Wi-Fi gateways, for which the coverage is only a few meters (ten meters at most). Thus, if a third-party terminal has detected such a beacon whose id entifier is included in the list from the first terminal, during the predetermined period of time, then the risk of infection of the user of this third-party terminal is further established.

The aforementioned identifiers of radio frequency beacons may typically be the SSIDs (for "Service Set Identifier") of access points. Moreover, since in general the geographical position of such access points is known, detection of these access points can contribute to obtaining the current geographical positions of the first terminal during the predetermined period of time, for example by triangulating the detection of different access points. In general, the above phrase "obtained by geolocation" denotes the obtaining of geographical position data by triangulation as well as by "conventional" geolocation of the GPS ("Global Positioning System") type.

Furthermore, the term "detected near" is understood to mean, for example, the fact that the signal power detected from a beacon, by the first terminal, exceeds a threshold.

In one embodiment, the estimation of the region at risk may be obtained by extrapolation from at least the geographical position data obtained by geolocation.

This may be for example a region around a cloud of points defined by geographical positions of the first terminal during the predetermined period of time or by a disc having a radius of several kilometers for example around an average position, or other, as will be seen below with reference to FIG. 4 discussed below.

In one embodiment, the abovementioned chosen criterion then comprises:
- the fact that a geographical position of the second terminal is located within the region at risk estimated by extrapolation, and
- the fact that an identifier of a radio frequency beacon detected near the second terminal is included in the list among the identifiers of the radio frequency beacons detected near the first terminal.

In such an embodiment, the second terminal stores at least one identifier of a radio frequency beacon detected near the second terminal during said period of time, said geographical position data of the second terminal being obtained by geolocation and/or by detection of a radio frequency beacon near the second terminal during at least said period of time, and:
- the second terminal ignores the notification if the geographical position of the second terminal during said period of time is outside the region at risk estimated by extrapolation, and
- if the geographical position of the second terminal is within the region at risk estimated by extrapolation, it is further verified that the identifier of the radio frequency beacon detected near the second terminal corresponds to an identifier of a radio frequency beacon in the list.

For the second terminal as for the first terminal, in the event of simultaneous detections of several radio frequency beacons near the terminal, the terminal stores the identifier of the radio frequency beacon detected having a signal of maximal power or, as indicated above, the identifier of at least one of said radio frequency beacons simultaneously detected for which the power of the detected signal exceeds a predetermined power threshold.

In a first embodiment, if the geographical position of the second terminal during said period of time is within the region at risk estimated by extrapolation, the second terminal receives the beacon identifiers from the list in order to carry out the verification at the second terminal.

In a second alternative embodiment, if the geographical position of the second terminal during said period of time is within the region at risk estimated by extrapolation, the second terminal sends to the server said at least one identifier of a radio frequency beacon detected near the second terminal during said period of time, in order to carry out the verification at the server.

This second embodiment makes it possible to avoid communicating to the second terminal the identifiers of the beacons detected by the first terminal and thus to protect the personal data of the user of the first terminal.

In one embodiment, the list from the first terminal comprises the successive geographical position data of the first terminal, with respective corresponding timestamps for when the first terminal occupied said geographical positions, and the estimation of said region at risk of infection comprises a determination of a route traveled by the first terminal during said predetermined period, and in the event of a coincidence, according to the chosen criterion, between the geographical position of the second terminal and the route traveled by the first terminal, the human-machine interface connected to the second terminal is activated in order to inform the second user of a risk of infection.

The region at risk that is estimated from this route traveled by the first terminal is illustrated by way of example in the upper part of FIG. 4, discussed below.

In one embodiment, the aforementioned method further comprises:
- determining successive geographical positions of the second terminal, and storing a second list of geographical position data for said geographical positions of the second terminal with respective corresponding timestamps for the determinations of the geographical positions of the second terminal,
- and comparing the data of the first list with the data of the second list, to verify whether at least one geographical position of the second terminal in the second list is coincident, according to the chosen criterion, with a geographical position of the first terminal in the first list, at respective timestamps that are close according to a second predetermined criterion, and in such case activating the human-machine interface in order to inform the second user of a risk of infection.

The "second predetermined criterion" may be such that the respective timestamps are identical or differ with a positive difference (the timestamp of the second terminal minus that of the first terminal) that is less than a threshold duration. This threshold duration may correspond, for example, to a maximum duration of the survival of the disease-causing virus on an inert surface (for example 48 hours in the case of COVID19).

In one embodiment, the first terminal sends a server a request for confirmation of the infection data of the first user, together with contact data for a healthcare professional's terminal listed on the server, and the server confirms the infection data if the server also receives a valid code from the healthcare professional's terminal.

Such an embodiment makes it possible for a healthcare professional to confirm the infection of the user of the first terminal, before push notifications to third-party terminals are triggered.

In an embodiment illustrated in FIG. 5, discussed below, the region at risk is estimated by:
a) calculating an average position occupied by the first terminal during said period of time, in order to determine a first barycenter associated with a first area at risk (for example a disc having a radius of several kilometers around the first barycenter),
b) excluding, from the calculation of the average, any positions in the list that are located beyond a threshold distance (for example a fixed threshold distance or several standard deviations) around the first barycenter, and repeating the calculation of the average without the excluded positions in order to refine the determination of the first barycenter.

Figure 5:
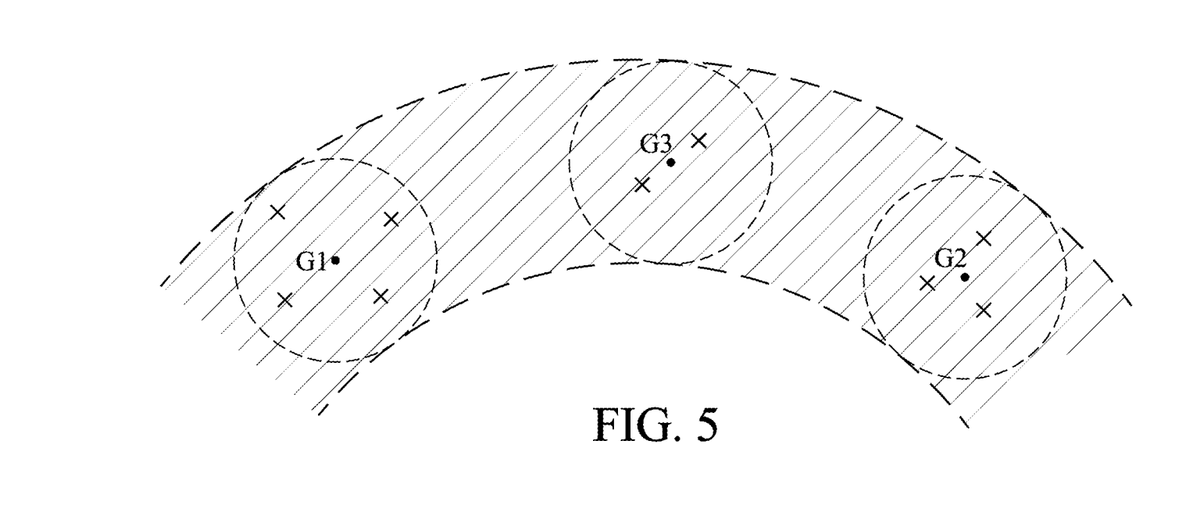
FIG. 5 shows a second embodiment for determining the region at risk, based on the estimation of successive averages of the positions of terminal T1.

In such an embodiment, in order to determine a plurality of areas at risk, operations a) and b) are repeated with the excluded data in order to identify at least a second barycenter associated with a second area at risk (and so on, in order to achieve a general region shape as illustrated in FIG. 5 by oblique hatching).

This description also relates to a computer program comprising instructions for implementing the above method, when said instructions are executed by a processor of a processing circuit.

It also relates to a non-transitory storage medium readable by a processing circuit, in which is stored a computer program for implementing the above method when this program is executed by a processor of the processing circuit.

The instructions of this program may be distributed across the aforementioned terminals and the server, and, on the terminals, part of this program may be in the form of an application installed on the terminals.

This description also relates to a system for implementing the above method, comprising the first mobile terminal, the second terminal, and the server, configured at least for estimating the region at risk of infection.

This description also relates to a server for implementing the method, and configured in particular at least for estimating the region at risk of infection.

This description also relates to a mobile terminal for implementing the method, in particular configured at least for sending to the server the data from the list of geographical positions of the mobile terminal and the infection data for the user of the mobile terminal.

This description also relates to a terminal for implementing the method, in particular configured at least for activating said human-machine interface in order to inform the terminal's user of a risk of infection, in the event of a coincidence, according to the chosen criterion, between the geographical position of the terminal and the region at risk.

BRIEF DESCRIPTION OF THE DRAWINGS

Other features, details, and advantages will become apparent upon reading the detailed description below, and upon analyzing the appended drawings, in which.

DETAILED DESCRIPTION OF CERTAIN ILLUSTRATIVE EMBODIMENTS

Figure 1:
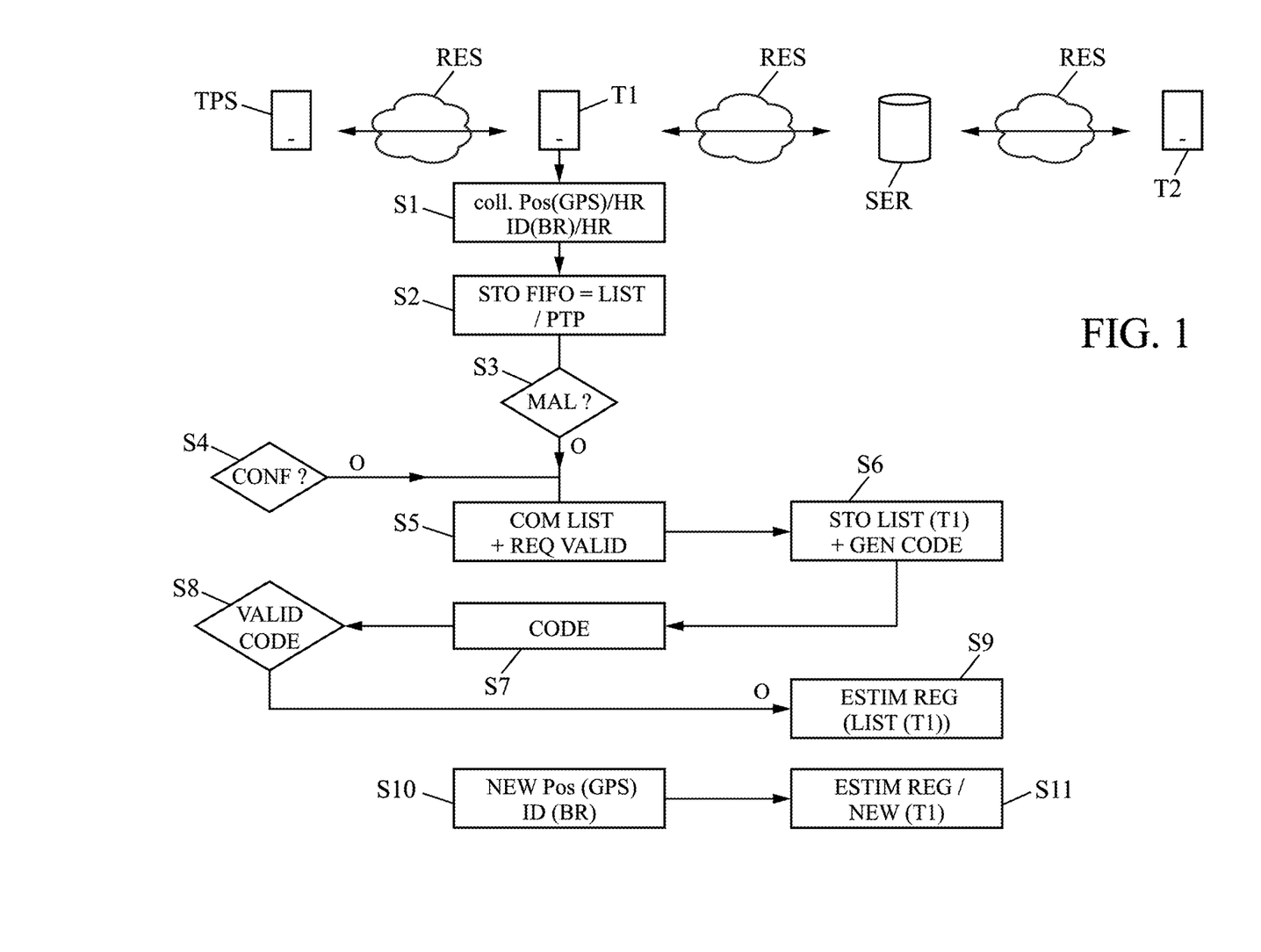
FIG. 1 shows a system for implementing the present description, as well as the first steps of a method in one exemplary embodiment, in which the server SER collects, from the mobile terminal T1 of the infected person, at least the person's geographical position data in order to estimate a region at risk of infection.

Referring to FIG. 1, a system for implementing the method presented above may comprise:
- a server SER, in particular for estimating the region at risk of infection,
- the mobile terminal T1 of an infected person,
- one or more terminals T2 available to third parties wishing to be informed of the spread of the disease, in order to be able to take measures to protect themselves and their loved ones,
- and, in the example shown, the terminal of a healthcare professional TPS.

These various devices are linked by one or more communication networks NET.

During a first step S1, mobile terminal T1 collects the various geographical positions that it successively occupies and stores in memory the data of these geographical positions along with respective corresponding timestamps HR in step S2. In one particular embodiment, terminal T1 further collects and stores, in memory, identifiers ID(BR) of radio frequency beacons detected by terminal T1 on its route, with corresponding timestamps HR.

The collection of the identifiers ID(BR) may be exhaustive (i.e. the identifiers of all detected radio frequency beacons are stored). However, advantageously, only the identifiers of the radio frequency beacons deemed to be the most relevant among the detected beacons are collected and stored. For example, if terminal T1 detects several radio frequency beacons simultaneously, terminal T1 may only collect the identifiers of the beacons having maximal signal power (for example N beacons having the greatest signal power), or may only collect the identifiers of beacons for which the power of the signal received by terminal T1 is greater than a certain threshold, doing this in order to avoid cluttering the storage memory of terminal T1 with too much data.

The geographical position data may be obtained by conventional means such as geolocation (GPS) by means of a geolocation module of terminal T1, or triangulation on several access points to the cellular network, or, additionally or alternatively, based on presumably known positions of the radio frequency beacons that terminal T1 detects during its movement.

All of these data (geographical positions Pos(GPS) and identifiers of detected radio frequency beacons ID(BR)) are stored with corresponding successive timestamps HR, in the form of a list LIST, in a FIFO (First In/First Out) type of memory, always with the view of not filling up the storage memory of terminal T1. Indeed, this type of storage is well suited for storage according to a sliding time window, this time window possibly corresponding for example to the incubation period of the disease plus several days. It is thus possible to determine the route of mobile terminal T1 over a predetermined period of time PTP, and then to estimate a region at risk of infection based on this route, as will be seen below with reference to FIGS. 4 and 5 described below.

In order to collect and store these various data, a specific application is installed on terminal T1, this application being able to be executed as a background task (without its execution being visible to its user).

Referring now to step S3 of FIG. 1, here, when the user of mobile terminal T1 begins to feel the symptoms of the disease DISEASE (arrow Y exiting test S3), the user can consult a healthcare professional (bearer of terminal TPS). In step S4 the healthcare professional confirms the infection of the user of terminal T1 (arrow Y exiting test S4).

The user of terminal T1 then uses a human-machine interface of his or her terminal T1 to execute a routine of the aforementioned application, consisting of declaring his or her illness to the server SER while transmitting data from the list of geographical positions and the identifiers of radio frequency beacons in step S5, as well as infection data relating to infection of the user by the disease.

In step S6, the server SER then stores the data from the list specific to mobile terminal T1, which will be used as described below.

In one particular embodiment, described by the example illustrated in FIG. 1, in addition to the data in this list, terminal T1 also sends a request REQ for confirmation of the diagnosis of the healthcare professional, to the server SER.

Upon receiving the request REQ, the server SER generates a code CODE which it sends back to terminal T1 in step S7. This code may be for example a sequence of characters and/or numbers that the user of terminal T1 shows or communicates orally to the healthcare professional. In step S8, if the healthcare professional does indeed confirm the infection of the user of terminal T1, he or she sends the aforementioned code via his or her terminal TPS to the server SER. To this end, a specific application is also installed on the terminal TPS of the healthcare professional and the healthcare professional launches the execution of this application when he or she confirms the infection of the patient using terminal T1.

In step S9, the server SER receives the code CODE from the terminal TPS of the healthcare professional and verifies:
  on the one hand, that the code is indeed sent from a terminal recognized as being that of a healthcare professional, and,
  on the other hand, that this code is indeed valid for terminal T1, so that the data from the list received from terminal T1 can indeed be used to estimate the region at risk of infection REG.

The data from the list specific to terminal T1 can then be used to estimate the region at risk of infection. As will be seen below, this region is not determined simply by the exact points of the geographical positions of terminal T1, but concerns a broader region including these points. Such an implementation makes it possible in particular to avoid the risk of disclosing the exact route of a user's terminal (typically in order to protect the user's personal data).

The method may then optionally continue with the acquisition, in step S10, of new geographical position data for terminal T1 and of identifiers of successively detected radio frequency beacons. Such an implementation makes it possible to update the estimate of the region at risk in step S11.

Figure 2:
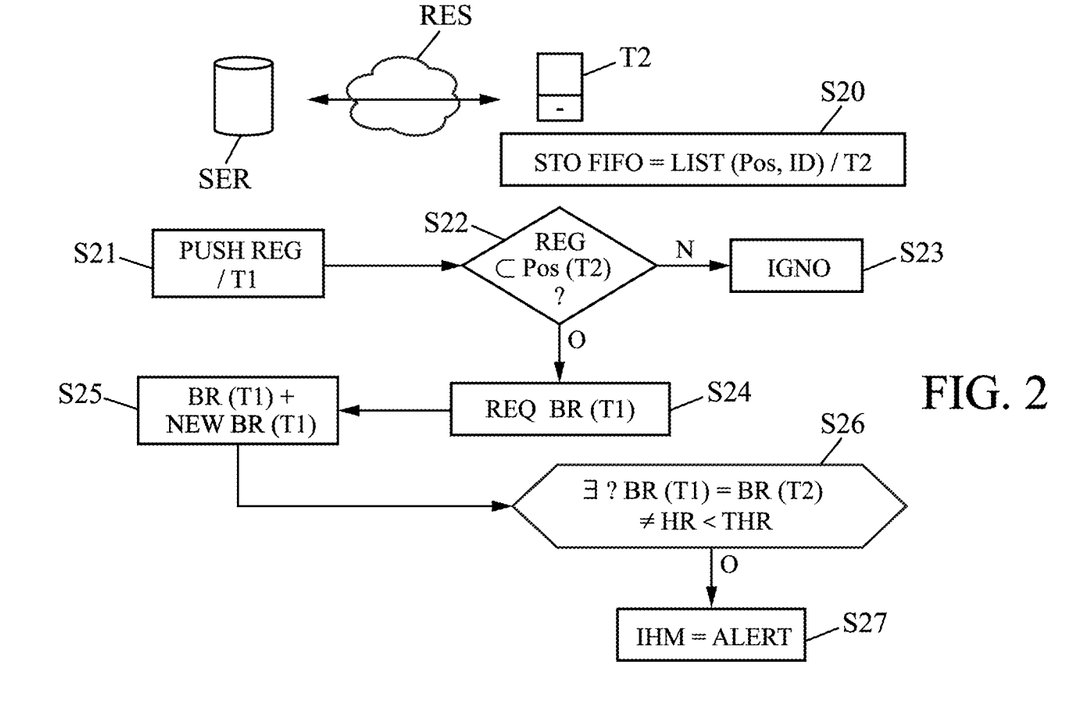
FIG. 2 shows the sequence of steps of the method of FIG. 1, in which the terminal T2 of a third party determines in particular whether it is or has been within the region at risk, according to a first embodiment.

Referring now to FIG. 2, third-party terminals T2 are also running a specific application in order to be kept informed of the spread of the disease, and thus be able to limit infection, as follows. These may but do not necessarily include mobile terminals (e.g. smartphones) in which the specific application has been installed. In step S20, each terminal T2 also stores in a memory in FIFO mode the data from a list of geographical positions occupied by terminal T2, as well as identifiers of radio frequency beacons detected by terminal T2 during a predetermined period of time PIP (typically the incubation time of the disease plus a few days, as described above for terminal T1), similar to what is done by terminal T1.

In step S21, after having estimated the region at risk specific to terminal T1 (and optionally after having also confirmed the code specific to a user of this mobile terminal T1), the server SER sends a notification in "push" mode to all terminals T2 in which the aforementioned application is installed, this notification comprising information about the region at risk of infection which has been estimated by the server SER for terminal T1. Each terminal T2 receiving this notification determines in step S22 whether, in the list of its geographical positions stored in step S20, at least one of the stored positions is included in the region at risk. If such is not the case (arrow N exiting test S22), terminal T2 ignores this notification in step S23 and stands ready to receive any other notifications. Otherwise (arrow Y exiting test S22), in a first embodiment illustrated in FIG. 2, terminal T2 requests from the server SER the identifiers of radio frequency beacons detected by terminal T1 during the predetermined period of time PIP and possibly new identifiers acquired in step S10 of FIG. 1. The server SER then sends these identifiers to terminal T2 in step S25, and terminal T2 can then determine in step S26 whether there is at least one common radio frequency beacon identifier in the list for terminal T1 and the list stored by terminal T2, in particular at an identical or close timestamp. This situation means that terminal T2 has detected the same radio frequency beacon as terminal T1 at the same timestamp or at a close timestamp.

These radio frequency beacons are, for example, terminals offering Wi-Fi, Bluetooth, or other ("hotspot" type) access, or even residential gateways acting as Wi Fi access points. The range of such a radio frequency beacon is generally therefore a few meters (about ten meters at most). If terminal T2 has detected the same radio frequency beacon as terminal T1 at the same timestamp, then the user of terminal T2 has crossed paths with the user of terminal T1 (who is infected and within the incubation period) by a distance limited to a few meters.

The risk of infection of the user of terminal T2 is then established. Here, the term "close timestamp" means that the timestamps are identical or differ with a positive difference (the timestamp of terminal T2 minus that of terminal T1) that is less than a threshold duration THR which may correspond for example to the lifespan of the disease-causing virus on an inert surface (for example estimated to be up to 48 hours for COVID19 on a metal surface).

In this case, in step S27, the application installed on terminal T2 then activates the human-machine interface of terminal T2 to inform the user of terminal T2 of a risk of infection. Note that terminal T2 only accesses the beacon identifier data if the presence of terminal T2 in the region at risk is confirmed; this is to protect the personal data of the user of terminal T1. In addition, confirmation of the beacon identifiers in step S26 is carried out by terminal T2 without the knowledge of its user and the user is only alerted when there is activation of the human-machine interface in step S27, which is conditional upon detecting a common beacon identifier between the lists of terminals T1 and T2. Such an implementation makes it possible to protect the personal data of the user of terminal T1 as much as possible.

Figure 3:
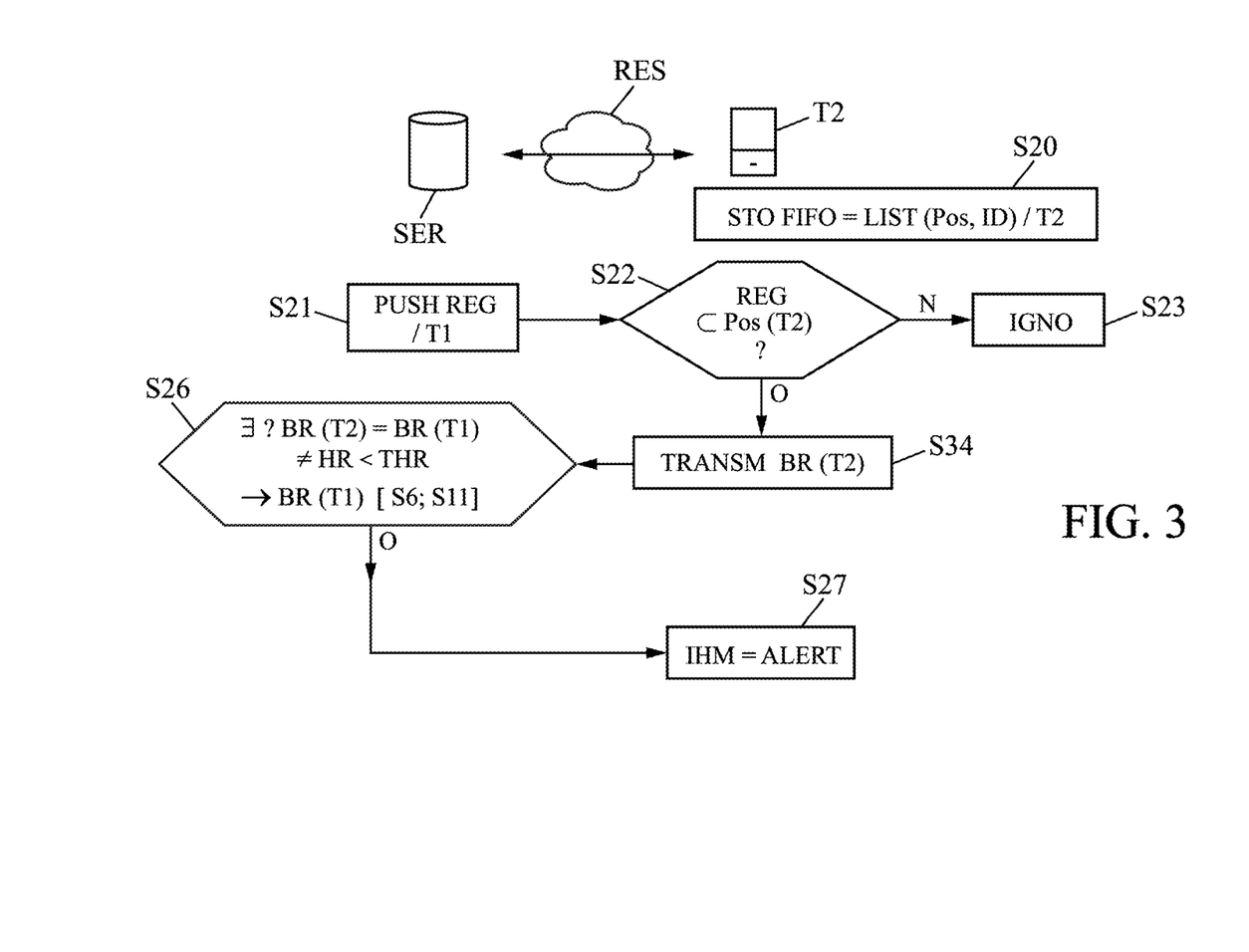
FIG. 3 shows the following steps of the method of FIG. 1, in which the server SER determines for the terminal T2 of the third party in particular whether this terminal T2 is or has been within the region at risk, according to a second embodiment.

Referring now to FIG. 3, the same reference numbers for steps as used in FIG. 2 denote the same (or similar) steps. Here, terminal T2 transmits the identifiers of radio frequency beacons from its list to the server SER in step S34 if terminal T2 has previously identified that at least one of the geographical positions in its list is located in the region at risk (arrow Y exiting test S22). In this case, the server SER performs test S26 for terminal T2, and if it is positive (arrow Y exiting test S26), the server SER sends to terminal T2 a message that the application installed on terminal T2 identifies in order to activate the human-machine interface of terminal T2 to alert its user of a risk of infection in step S27.

Such an embodiment makes it possible here to avoid providing terminal T2 with the identifiers of radio frequency beacons detected by terminal T1, and thus to completely protect the personal data of the user of terminal T1. In addition, such an embodiment makes it possible to save resources of terminal T2, by leaving it up to the server SER to perform the comparisons of identifiers in step S26.

In one particular embodiment, the notifications including data concerning a region at risk of infection are sent to all terminals T2 in which the above specific application has been installed, the operator of the network NET having knowledge of this set of terminals T2. However, as this specific application, in the event of an epidemic, is intended to be deployed to a large number of terminals T2, it is possible to restrict the sends in push mode to a limited number of terminals T2 among all of the terminals having installed the application, in order to save bandwidth in the network NET. For this purpose, the terminals T2 can send to the server SER, for example periodically, an average geographical position they are currently occupying and the server SER can send the push notification only to those terminals T2 which have occupied an average geographical position included within the region at risk during the predetermined period of time.

Figure 4:
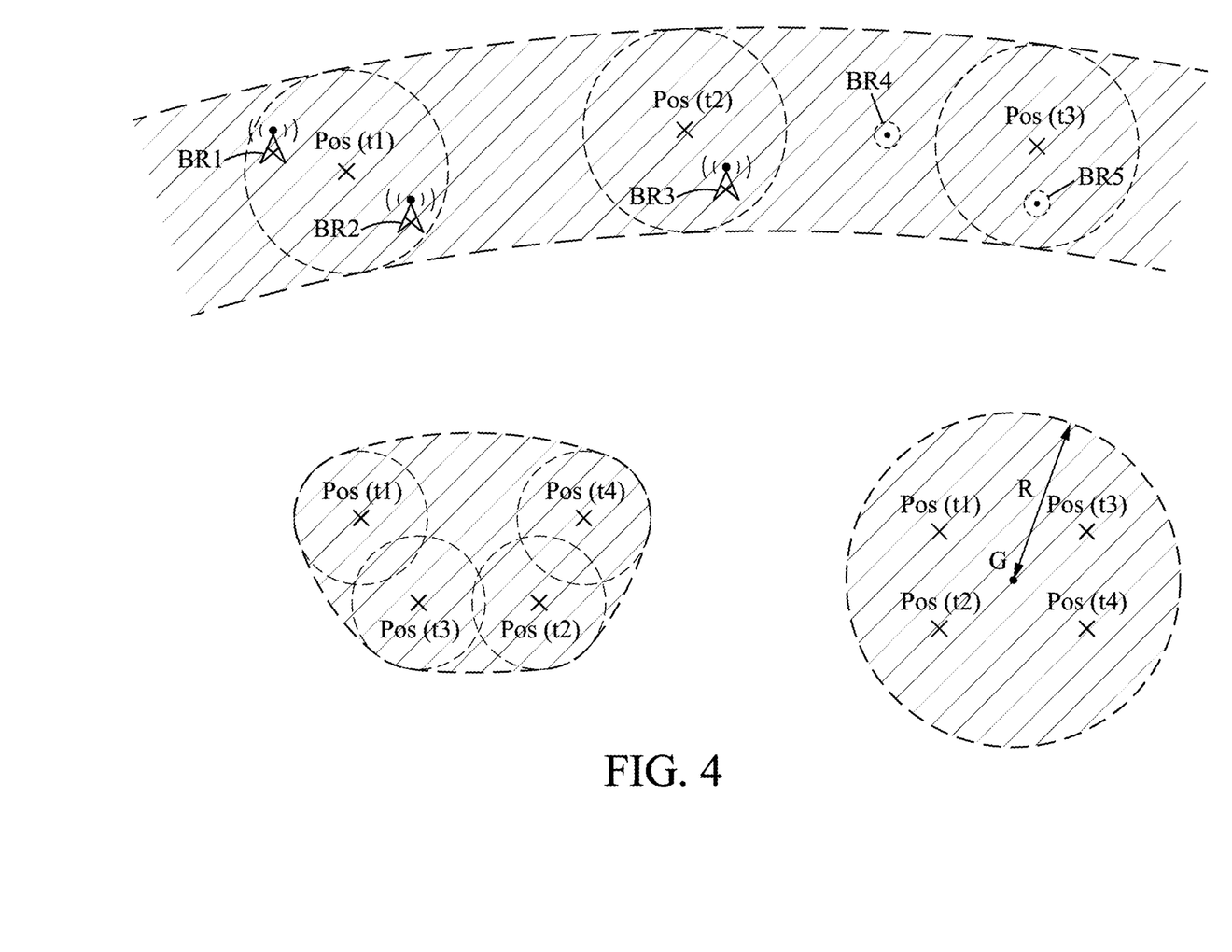
FIG. 4 shows a first exemplary embodiment for determining the region at risk, based on successive timestamps for positions of mobile terminal T1.

Reference is now made to FIG. 4 to describe possible embodiments for estimating the region at risk of infection. In the example presented in the upper part of FIG. 4, terminal T1 occupies various geographical positions over time: Pos(t1), Pos(t2), Pos(t3), etc., and detects various radio frequency beacons along this path BR1, BR2, BR3, BR4, BR5, etc. Terminal T1 stores these various positions and the identifiers of these beacons in memory (for example their SSID (for "Service Set Identifier") when the radio frequency beacon is a Wi-Fi access point) in order to construct the aforementioned list intended to be transmitted to the server SER.

In one embodiment illustrated at the top of FIG. 4, the server SER estimates the region likely to have been infected by the user of terminal T1 as follows:
 a radius (of a few hundred meters or kilometers) is assigned around each position Pos(t1), Pos(t2), Pos(t3), etc. of the list, thus constructing disc-shaped regions at risk of infection, and
 the various regions are connected by extrapolation, forming said general region at risk of infection (represented by oblique hatching in FIG. 4).

By way of illustration, for beacons BR4 and BR5, their range of detection by terminal T1 has been represented with dotted lines, to show that the range of their coverage area (a few meters) is much smaller than the area of the estimated region (a few kilometers wide). Of course, in FIG. 4 this aspect is not drawn to scale.

To avoid filling up the memory of terminal T1 and/or to save bandwidth in the network NET when terminal T1 communicates its data to the server SER, terminal T1 may periodically store its geographical position (or an average geographical position) and/or the beacon identifiers, for example every hour, or every half hour, depending on the desired degree of confidence related to the virulence of the disease for example.

Additionally or alternatively, the server SER itself may determine an average geographical position of terminal T1, per time interval t1, t2, t3, etc. and thus estimate a possible region of infection around this average position.

Indeed, by referring to the bottom left of FIG. 4, it appears that if terminal T1 has occupied successive geographical positions within a same general area, the region at risk of infection can be defined simply as within a predetermined radius around these geographical positions. This region may then appear as a closed "oval" around these positions as shown at the bottom left of FIG. 4, rather than as a "bent cylinder" as shown at the top of FIG. 4. In the example at the bottom left of FIG. 4, it is thus considered that the region at risk can be defined by a minimum radius (for example of a few kilometers) containing all the stored geographical positions of terminal T1 during the predetermined period of time.

At the bottom right of FIG. 4, an extreme situation has been illustrated in which the region at risk of infection is estimated simply:
 by calculating an average of the geographical positions, resulting in a barycenter G between these positions, and
 by assigning to this barycenter G a disc of predetermined radius R around the barycenter G.

In this case, the region at risk of infection is determined simply by the disc of radius R around the barycenter G. The data of the region at risk, inserted into the notification to be sent by the server SER to terminals T2, may simply then comprise the geolocation coordinates of the barycenter G and the radius R, advantageously associated with a timestamp specifying the date at which this region is considered to be at risk (i.e. the date when terminal T1 was also there).

It will thus be understood that the shape of the estimated region can be extrapolated with more or less accuracy, depending on the desired degree of confidence, in relation to the more or less contagious character of the epidemic.

Thus, in general, it is not the historical data of the geographical positions of the infected patient (user of terminal T1) which are pushed by the server SER to terminals T2 in step S21 (FIGS. 2 and 3), but instead a wider geographical region, defined by the server SER on the basis of the coordinates of the geographical positions in the list it has received from the terminal T1, over a general predetermined period of time PTP. This allows the use of push notification messages of small capacity, such as the notifications provided in a standard manner by mobile operating systems such as Android or iOS. The receiving terminals T2 then only have to run a first verification on a general region. For example, if the infected patient has traveled to a region corresponding to a city (Marseille for example), the terminals of users from another city who would receive this push notification simply ignore this notification. Terminal s T2 of Marseille users, on the other hand, and only these terminals, ask the server SER for details on the identifiers of beacons detected by terminal T1 in order to verify more closely whether they could have been near the terminal T1 of the infected patient.

Moreover, in the extreme case illustrated at the bottom right of FIG. 4, it is apparent that the storage of geographical position data and the association of timestamps is optional. Thus, to avoid saturating the memory of terminal T1 and/or to save bandwidth in the network NET when terminal T1 communicates its data to the server SER, terminal T1 may ultimately store timestamps only when they are linked to detection of a radio frequency beacon (in association with the beacon identifiers).

Such an embodiment does not exclude identifying different areas traveled through by mobile terminal T1 over the predetermined period of time PTP. Indeed, with reference now to FIG. 5, the server SER can estimate the region at risk of infection as follows, by:
  calculating an average over all positions occupied by terminal T1, and excluding the positions which are distant by one or more standard deviations (or by a fixed distance) from the barycenter that this average represents in order to refine the position of the barycenter, and a first area at risk is thus determined around this first barycenter G1,
  repeating the preceding step of calculating the average, using the positions that were previously excluded, and thus determining the position of a new barycenter G2, and so on.

A succession of disc-shaped areas is thus obtained around respective barycenters G1, G2, G3, etc., and the region at risk of infection is determined by extrapolation between all of these areas.

Figure 6:
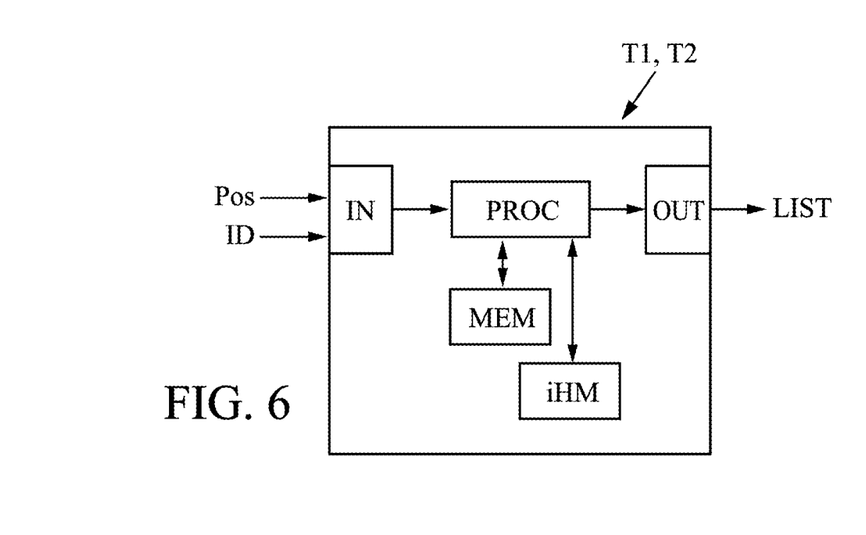
FIG. 6 schematically shows a processing circuit of a terminal T1 or T2 for implementing the aforementioned method, in one exemplary embodiment.

Referring now to FIG. 6, a processing circuit of one of terminals T1 or T2 is schematically illustrated, comprising:
  an input interface IN for receiving geographical position data Pos (typically provided by a geolocation module, for example of the GPS type, embedded in this terminal T1 or T2) and identifiers ID of detected radio frequency beacons (typically provided by a radio transmission/reception module of this same terminal T1 or T2, after this module has detected the radio frequency signals emitted by these beacons and deduced the identifiers ID from these signals),
  a processor PROC connected to the input interface for possibly filtering these data, and for controlling the storage of these data in:
  a memory MEM, this memory MEM also being able to store instructions of a computer program corresponding to the application installed on terminal T1 or T2.

Finally, the processing circuit may further comprise an output interface OUT for transmitting the data from the list LIST to the server SER (for example by means of the aforementioned radio transmission/reception module), as well as the human-machine interface HMI which can be activated in particular in order to warn the user of terminal T2 of a risk of infection, this interface HMI being able to be implemented in the form of a set of information displayed on a screen of terminal T1 or T2.

Figure 7:
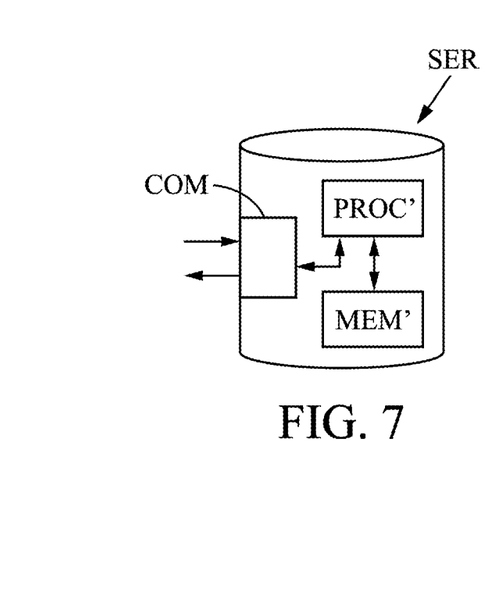
FIG. 7 schematically shows a processing circuit of a server SER for implementing the aforementioned method, in one exemplary embodiment.

Referring now to FIG. 7, the server SER may itself comprise a processing circuit including:
  an interface COM for communicating with terminals T1, T2 via the network NET, in particular in order to receive the list data from these terminals,
  a processor PROC', in particular for estimating the region at risk of infection, and
  a working memory MEM and/or a memory for storing the instructions of a computer program for implementing the method described above.

This description is not limited to the embodiments described above, but also encompasses other variants.

For example, the aforementioned second terminal may or may not be mobile. It may be for example a fixed access terminal such as a residential gateway, which the first terminal, being mobile, has been connected to or which the first terminal has simply detected as being nearby. In this case, the method takes place in the same manner as described above, the radio frequency beacon identifier stored by the second terminal being the identifier of the gateway itself. The gateway can then receive an alert message from the server SER and be connected to a human-machine interface (for example a television or computer screen connected to the gateway) in order to display a message indicating to the gateway's user a risk of infection.

Furthermore, the second verification presented above, based on the comparison of beacon identifiers, may be optional in certain embodiments which are particularly protective in terms of personal data and economical in terms of network resources, where only the first verification of a coincidence between the geographical position data of a terminal T2 and a region at risk determined from the geographical positions of terminal T1 is carried out. This second verification may or may not be implemented, depending for example on the virulence of the contagious disease and/or depending on the desired degree of confidence for detecting the infection.

Furthermore, an embodiment has been described above in which the transmission of the list of positions of terminal T1 to the server SER is only carried out if the user of terminal T1 declares himself or herself as being infected. Alternatively, an implementation may consist of terminal T1 and/or terminal T2 regularly transmitting their position data without this infection condition, so that the server SER already has these data for estimating the region to risk as soon as it receives infection information from terminal T1.

The invention claimed is:

1. A method, implemented by networked devices, for assisting in controlling the spread of a contagious disease, the method comprising:
  upon receiving data relating to infection by a disease of a first user of a first mobile terminal, obtaining a list comprising at least successive geographical position data of the first terminal over a predetermined period of time, and estimating from the list at least one region at risk of infection by the first user; and
  for a second terminal available to a second user:
    obtaining at least one geographical position datum of the second terminal during at least the period of time, and comparing the geographical position of the second terminal to the region at risk by means of the geographical position datum of the second terminal, and
    in the event of a coincidence, according to a chosen criterion, between the geographical position of the second terminal and the region at risk, activating a human-machine interface connected to the second terminal in order to inform the second user of a risk of infection,
  wherein the list comprises the successive geographical position data of the first terminal, with respective corresponding timestamps for when the first terminal occupied the geographical positions, and the estimation of the region at risk of infection comprises a determination of a route traveled by the first terminal during the predetermined period, and in the event of a coincidence, according to the chosen criterion, between the geographical position of the second terminal and the route traveled by the first terminal, the human-machine interface connected to the second terminal is activated in order to inform the second user of a risk of infection.

2. The method according to claim 1, wherein:
a server obtains the infection data from the first user with the list of successive geographical position data of the first terminal in order to estimate the region at risk, and sends to the second terminal a notification comprising at least one datum relating to the region at risk; and
as the second terminal stores its geographical position data for at least the period of time, the second terminal:
  ignores the notification if there is no coincidence between its geographical position during the period of time and the region at risk, or
  activates the human-machine interface in the event of a coincidence, according to the chosen criterion, between its geographical position during the period of time and the region at risk.

3. The method according to claim 1, wherein the first terminal is configured for:
  storing in memory the list comprising the successive geographical position data of the first terminal over the predetermined period of time, according to a "first-in first-out" type of mode; and
  sending the infection data of the first user to a server, along with the data from the stored list.

4. The method according to claim 1, wherein the list comprises:
  successive geographical position data of the first terminal, obtained by geolocation; and
  respective identifiers of radio frequency beacons detected near the first terminal.

5. The method according to claim 1, wherein the estimation of the region at risk is obtained by extrapolation from at least the geographical position data obtained by geolocation.

6. The method according to claim 1, wherein the chosen criterion comprises:
  a geographical position of the second terminal within the region at risk estimated by extrapolation; and
  an identifier of a radio frequency beacon detected near the second terminal, which is included in the list among the identifiers of the radio frequency beacons detected near the first terminal.

7. The method according to claim 1, wherein the second terminal stores at least one identifier of a radio frequency beacon detected near the second terminal during the period of time, the geographical position data of the second terminal being obtained by geolocation and/or by detection of a radio frequency beacon near the second terminal during at least the period of time, and:
  the second terminal ignores the notification if the geographical position of the second terminal during the period of time is outside the region at risk estimated by extrapolation; and
  if the geographical position of the second terminal is within the region at risk estimated by extrapolation, it is also verified that the identifier of the radio frequency beacon detected near the second terminal corresponds to an identifier of a radio frequency beacon in the list.

8. The method according to claim 7, wherein, in the event of simultaneous detections of several radio frequency beacons near the second terminal, the second terminal stores the identifier of the radio frequency beacon detected having a signal of maximal power or the identifier of at least one of the radio frequency beacons simultaneously detected for which the power of the detected signal exceeds a determined power threshold.

9. The method according to claim 7, wherein, if the geographical position of the second terminal during the period of time is within the region at risk estimated by extrapolation, the second terminal receives the beacon identifiers from the list in order to carry out the verification at the second terminal, or sends to a server the at least one identifier of a radio frequency beacon detected near the second terminal during the period of time, in order to carry out the verification at the server.

10. The method according to claim 1, further comprising:
  determining successive geographical positions of the second terminal, and storing a second list of geographical position data for the geographical positions of the second terminal with respective corresponding timestamps for the determinations of the geographical positions of the second terminal;
  and comparing the data of the first list with the data of the second list, to verify whether at least one geographical position of the second terminal in the second list is coincident, according to the chosen criterion, with a geographical position of the first terminal in the first list, at respective timestamps that are close according to a second predetermined criterion, and in such case activating the human-machine interface in order to inform the second user of a risk of infection.

11. The method according to claim 1, wherein the region at risk is estimated by:
  a) calculating an average position occupied by the first terminal during the period of time, in order to determine a first barycenter associated with a first area at risk; and
  b) excluding, from the calculation of the average, any positions in the list that are located beyond a threshold distance around the first barycenter, and repeating the calculation of the average without the excluded positions in order to refine the determination of the first barycenter.

12. A server for implementing the method according to claim 1, configured at least for estimating the region at risk of infection.

13. A mobile terminal for implementing the method according to claim 1, configured at least for sending to a server the data from the list of geographical positions of the mobile terminal and the infection data for the user of the mobile terminal.

14. A system for implementing the method according to claim 1, comprising the first mobile terminal, the second terminal, and a server, configured at least for estimating the region at risk of infection.

15. A non-transitory storage medium readable by a processor, the medium storing program code instructions of a computer program for implementing the method according to claim 1, when the computer program is executed by the processor.

16. A method, implemented by networked devices, for assisting in controlling the spread of a contagious disease, the method comprising:
  upon receiving data relating to infection by a disease of a first user of a first mobile terminal, obtaining a list comprising at least successive geographical position data of the first terminal over a predetermined period of time, and estimating from the list at least one region at risk of infection by the first user; and for a second terminal available to a second user:
  obtaining at least one geographical position datum of the second terminal during at least the period of time, and comparing the geographical position of the second terminal to the region at risk by means of the geographical position datum of the second terminal; and
  in the event of a coincidence, according to a chosen criterion, between the geographical position of the second terminal and the region at risk, activating a human-machine interface connected to the second terminal in order to inform the second user of a risk of infection;

and wherein the method further comprises:
  determining successive geographical positions of the second terminal, and storing a second list of geographical position data for the geographical positions of the second terminal with respective corresponding timestamps for the determinations of the geographical positions of the second terminal; and
  comparing the data of the first list with the data of the second list, to verify whether at least one geographical position of the second terminal in the second list is coincident, according to the chosen criterion, with a geographical position of the first terminal in the first list, at respective timestamps that are close according to a second predetermined criterion, and in such case activating the human-machine interface in order to inform the second user of a risk of infection.

17. The method according to claim 16, wherein the list comprises:
  successive geographical position data of the first terminal, obtained by geolocation; and
  respective identifiers of radio frequency beacons detected near the first terminal.

18. The method according to claim 16, wherein the estimation of the region at risk is obtained by extrapolation from at least the geographical position data obtained by geolocation.

19. The method according to claim 16, wherein the chosen criterion comprises:
  a geographical position of the second terminal within the region at risk estimated by extrapolation; and
  an identifier of a radio frequency beacon detected near the second terminal, which is included in the list among the identifiers of the radio frequency beacons detected near the first terminal.

* * * * *